(12) United States Patent
Olson et al.

(10) Patent No.: US 9,468,723 B2
(45) Date of Patent: Oct. 18, 2016

(54) MEDICAMENT DELIVERY DEVICE

(71) Applicant: SHL Group AB, Nacka Strand (SE)

(72) Inventors: Stephan Olson, Stockholm (SE); Slobodan Stefanov, Deerfield Beach, FL (US)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 14/993,670

(22) Filed: Jan. 12, 2016

(65) Prior Publication Data

US 2016/0193416 A1    Jul. 7, 2016

Related U.S. Application Data

(63) Continuation-in-part of application No. 13/806,779, filed as application No. PCT/SE2011/050775 on Jun. 17, 2011, now Pat. No. 9,248,236.

(60) Provisional application No. 61/358,093, filed on Jun. 24, 2010.

(30) Foreign Application Priority Data

Jun. 24, 2010   (SE) ...................... 1050692

(51) Int. Cl.
*A61M 5/00*   (2006.01)
*A61M 5/315*   (2006.01)
(Continued)

(52) U.S. Cl.
CPC .......... *A61M 5/3158* (2013.01); *A61M 5/2033* (2013.01); *A61M 5/3213* (2013.01)

(58) Field of Classification Search
CPC ...... A61M 5/2033; A61M 5/24; A61M 5/28; A61M 5/31501; A61M 5/31511

USPC ........................................... 604/232
See application file for complete search history.

(56) References Cited

U.S. PATENT DOCUMENTS 8,398,593 B2 *   3/2013  Eich ................. A61M 5/31583
                                                    604/131
9,248,236 B2    2/2016  Olson
(Continued)

FOREIGN PATENT DOCUMENTS

CH   WO 2011032731 A1 *   3/2011  .......... A61M 5/2033
GB       2443390 A           5/2008
(Continued)

OTHER PUBLICATIONS

Swedish Patent Office, Int'l Search Report in PCT/SE2011/050775, Oct. 11, 2011.
(Continued)

*Primary Examiner* — Jason Flick
(74) *Attorney, Agent, or Firm* — Piedmont Intellectual Property

(57) ABSTRACT

A medicament delivery device includes a housing; a carrier for a medicament container, the carrier being slidable in the housing; a trigger unit; a cover unit coaxial and slidable in the housing; a release mechanism configured to be actuated partly by the trigger unit and partly by movement of the cover unit; a preloaded drive unit releasably connected to the carrier and controlled by the release mechanism for advancing the carrier to a predetermined proximal position in relation to the housing, the preloaded drive unit having a plunger rod and a helical drive spring disposed within the plunger rod, with at least one end of the helical drive spring configured to interact with an interior of the plunger rod; and a braking mechanism between the preloaded drive unit and the release mechanism configured to control a speed of the preloaded drive unit when advancing the slidable stopper within the container.

8 Claims, 7 Drawing Sheets

(51) Int. Cl.
*A61M 5/20* (2006.01)
*A61M 5/32* (2006.01)

(56) References Cited

U.S. PATENT DOCUMENTS

2005/0101919 A1* 5/2005 Brunnberg .......... A61M 5/2033
604/197
2010/0114038 A1* 5/2010 Sams .................. A61M 5/2033
604/211

FOREIGN PATENT DOCUMENTS

WO    2005/044348 A1    5/2005
WO    2009/105908 A1    9/2009
WO    2011/032731 A1    3/2011

OTHER PUBLICATIONS

Swedish Patent Office, Written Opinion in PCT/SE2011/050775, Oct. 11, 2011.

* cited by examiner

MEDICAMENT DELIVERY DEVICE

This application is a continuation-in-part of U.S. patent application Ser. No. 13/806,779 filed on Dec. 23, 2012, which is a national-phase of International Application PCT/SE2011/050775 filed on Jun. 17, 2011, which claims the benefit of the filing date of U.S. Provisional Application 61/358,093 filed on Jun. 24, 2010, and which claims priority from Swedish Application 1050692-1 filed on Jun. 24, 2010.

TECHNICAL AREA

This invention relates to a medicament delivery device comprising a preloaded drive unit for delivering a dose of medicament and more particularly to a braking mechanism for controlling the speed of the preloaded drive unit.

BACKGROUND

There are many medicament delivery devices on the market that can perform a number of functions automatically.

One such medicament delivery device, disclosed in International Publication WO 2005/044348, is capable of a penetration sequence, an injection sequence, and thereafter a withdrawal sequence when a user has activated the device by first pressing it against an injection site and thereafter pressing an actuation button.

The device has been successful and is on the market for a number of different drugs for treatment of different diseases. The device uses a drive spring for both the penetration sequence as well as the subsequent injection sequence. For some drugs, it is desirable that the spring is as weak as possible in order that the sequences shall not be performed too fast and at the same time ensure that the medicament container is properly emptied, i.e., that the stopper is moved to the proximal end position inside the medicament container. Even so, it has been found that the injection sequence preferably should be performed even slower in order not to cause pain and discomfort to the user. There is thus room for improvements of an otherwise well-functioning medicament delivery device.

SUMMARY

An object of the present invention is to remedy the drawbacks of the state of the art devices. That object can be obtained by a medicament delivery device according to the features of the embodiments described in this application.

According to one aspect of the invention, a medicament delivery device includes an elongated housing; a carrier configured to house a medicament container to which a medicament delivery member is attached, where the carrier is slidably accommodated within the housing; a trigger unit having an actuator button and an actuator connected to each other; a cover unit coaxially and slidably disposed in the housing; a release mechanism configured to be actuated partly by the operation of the trigger unit and partly by movement of the cover unit; a preloaded drive unit releasably connected to the carrier and controlled by the release mechanism for advancing the carrier to a predetermined proximal position in relation to the housing, wherein the preloaded drive unit comprises a plunger rod and a helical drive spring disposed within the plunger rod; at least one end of the helical drive spring is configured to interact with an interior of the plunger rod; and when the carrier reaches the predetermined proximal position, the drive unit becomes disconnected from the carrier for advancing a slidable stopper within the container and thereby dispensing the medicament; and a braking mechanism between the preloaded drive unit and the release mechanism configured to control a speed of the preloaded drive unit when advancing the slidable stopper within the container. The braking mechanism includes a helical groove on an outer surface of the plunger rod, and at least one inwardly directed protrusion of the actuator interactively connected to the helical groove by a non-positive connection such that advancement of the carrier to the predetermined position causes rotation of the plunger rod. A winding direction of the helical groove is opposite to a winding direction of the helical drive spring.

According to another aspect of the invention, the preloaded drive unit comprises a drive spring and a plunger rod.

According to yet another aspect of the invention, the braking mechanism comprises a first braking device on the outer surface of the plunger rod and a second braking device of the release mechanism interactively connected to each other by a non-positive connection.

According to a further aspect of the invention, the trigger unit comprises an actuator button and an actuator connected to each other.

According to yet a further aspect of the invention, the cover unit comprises a delivery member cover and an actuator sleeve connected to each other, wherein the actuator sleeve is coaxially and slidably arranged on the actuator.

According to another aspect of the invention, the release mechanism comprises annular inwardly directed ledges on flexible tongues of the actuator, and recesses on the outer surface of the plunger rod arranged to be engaged with each other for holding the drive unit in a preloaded state in which the drive unit is connected to the carrier by a carrier driver.

According to yet another aspect of the invention, the first braking device is at least one groove on the outer surface of the plunger rod and wherein the second braking device is at least one inwardly directed protrusion on the flexible tongues of the actuator.

According to a further aspect of the invention, the at least one groove comprise a number of sections forming a zig-zag shape.

According to yet a further aspect of the invention, the at least one groove has a helical extension around the plunger rod.

According to another aspect of the invention, the at least one groove has a pitch that can be modified during manufacturing for modifying the speed of the plunger rod.

According to yet another aspect of the invention, a section of the at least one groove at the proximal end of the plunger rod has a direction generally parallel with the longitudinal direction of the plunger rod.

According to yet another aspect of the invention, at least one end of the helical drive spring includes a tang that interacts with the interior of the plunger rod such that when the plunger rod rotates, the tang contacts the interior of the plunger rod. Each end of the helical drive spring can also include a respective tang.

There are several advantages with the present invention. Because of the plunger rod brake it is possible to use stronger drive springs without the drawback that the dose delivery is performed very fast, which otherwise would be the case with stronger drive springs. Thereby it is ascertained that the medicament container is properly emptied.

Further the control of the speed of the plunger rod is acting directly on the plunger rod by the at least one protrusion acting in the at least one groove. Thus a very efficient yet simple design is obtained. It is also rather easy to change the speed of the plunger rod by altering the pitch of the at least one groove. Since the force of the drive spring is low at the end of the injection sequence no braking action is needed and thus the most proximal groove section is preferably generally parallel with the extension of the plunger rod.

These and other aspects and advantages of the present invention will become apparent from the following detailed description of the invention and from the accompanying drawings.

BRIEF DESCRIPTION OF THE DRAWINGS

The invention will be understood by reading this description in conjunction with the drawings, in which.

DETAILED DESCRIPTION

Figure 1:
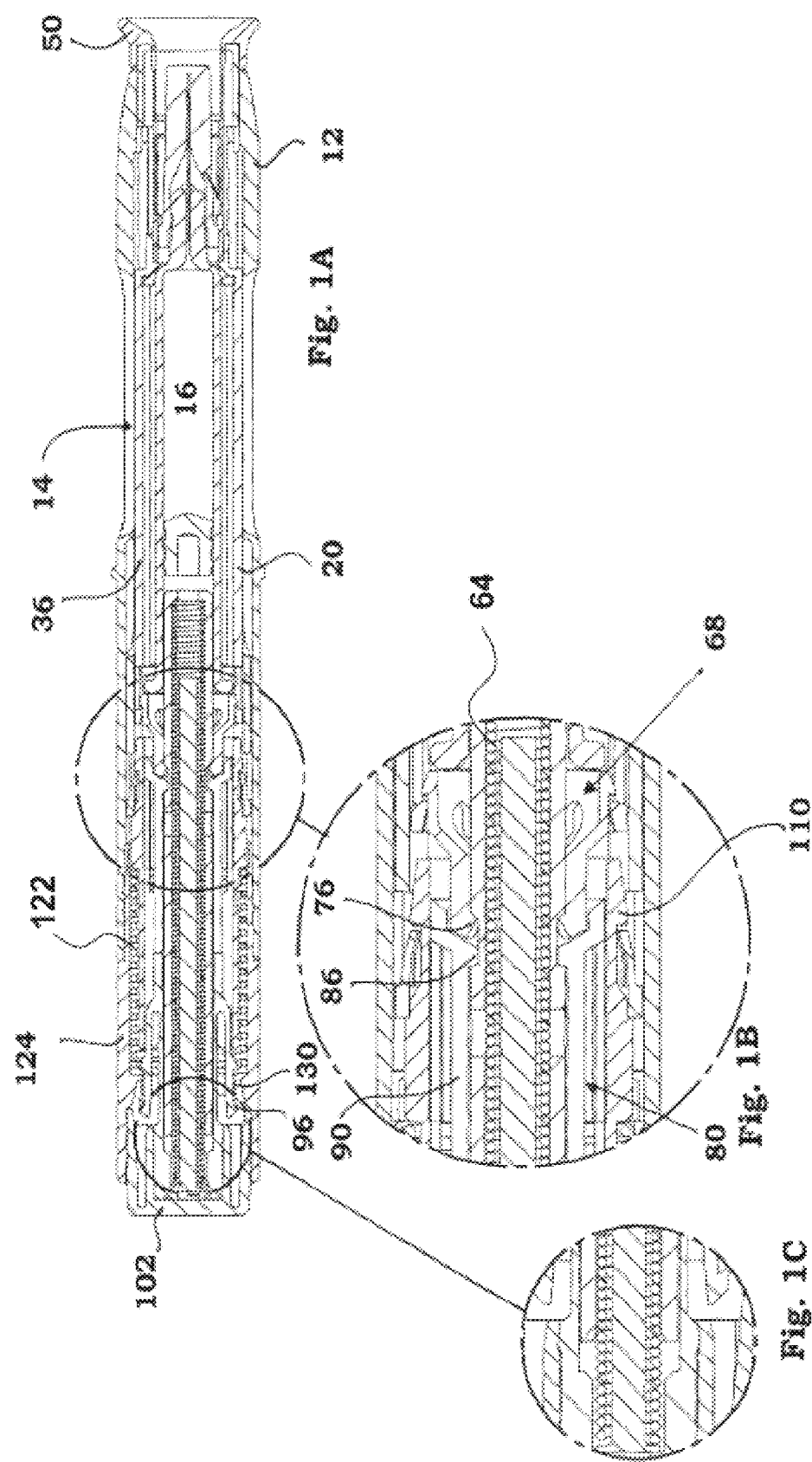
FIGS. 1A, 1B, 1C are cross-sectional views of a medicament delivery device according to the present invention.
Figure 2:
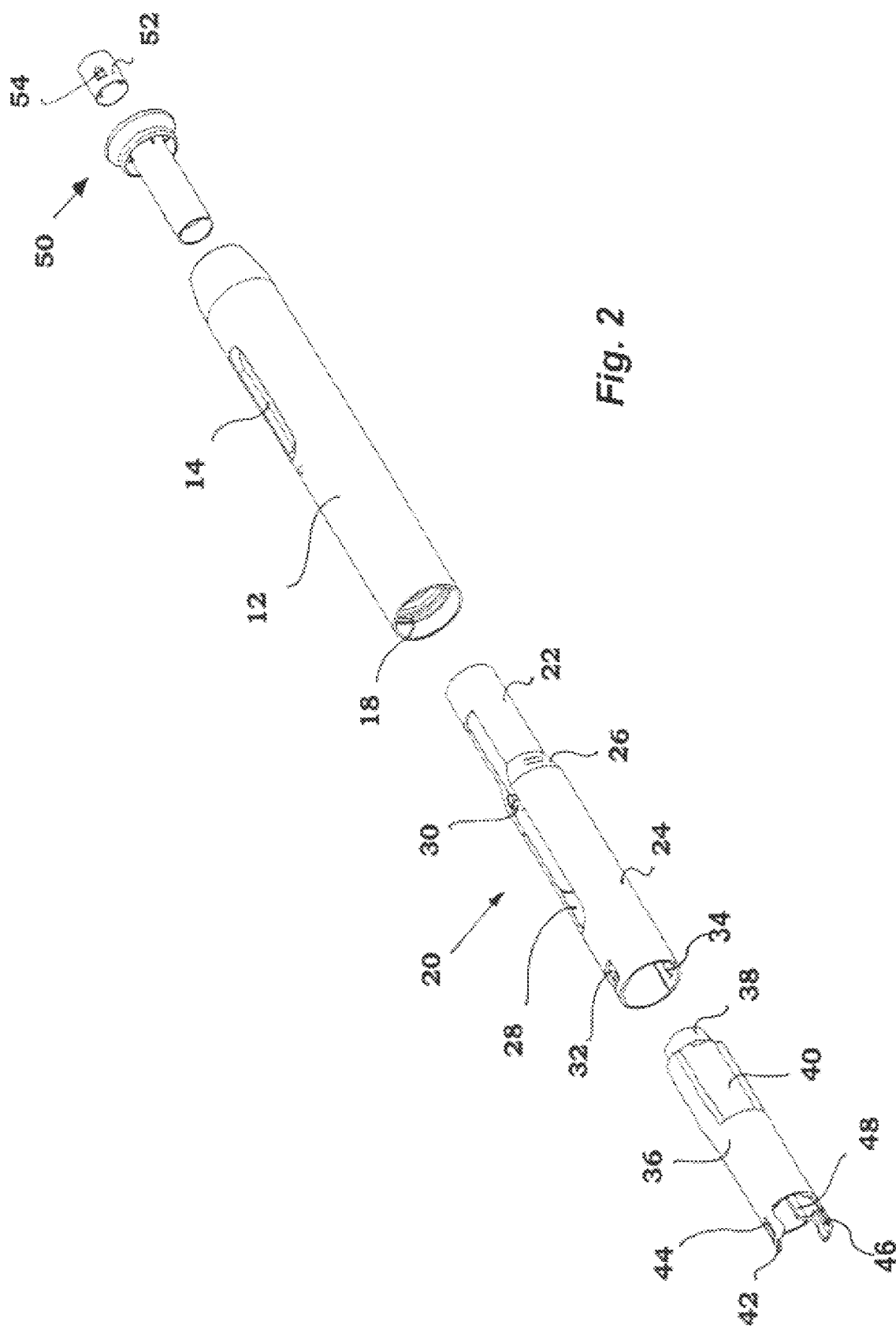
FIG. 2 is an exploded view of a proximal part of the device of FIG. 1.

In this application, the term "distal part/end" refers to the part/end of a medicament delivery device, or the parts/ends of the members thereof, which under use of the medicament delivery device is located farthest away from the medicament delivery site of the patient. Correspondingly, the term "proximal part/end" refers to the part/end of a medicament delivery device, or the parts/ends of the members thereof, which under use of the medicament delivery device is located closest to the medicament delivery site of the patient.

According to an aspect of the invention, the medicament delivery device comprises an elongated housing; a medicament container carrier 36 adapted to house a medicament container 16 to which a medicament delivery member is attached and wherein the carrier is slidably accommodated within the housing; a trigger unit; a cover unit coaxially and slidably arranged within the housing; a release mechanism adapted to be partly actuated by the operation of the trigger unit and partly actuated by the movement of the cover unit; a preloaded drive unit releasably connected to the medicament container carrier and controlled by the release mechanism for advancing firstly the medicament container carrier to a predetermined proximal position in relation to the housing and upon the carrier reaching the predetermined proximal position, the drive unit becomes disconnected from the carrier for advancing a slidable stopper within the container and thereby dispensing the medicament; and a braking mechanism acting between the preloaded drive unit and the release mechanism for controlling the speed of the preloaded drive unit when advancing the slidable stopper within the container.

The preloaded drive unit comprises a drive spring 64 and a plunger rod 60. The braking mechanism comprises a first braking device on the outer surface of the plunger rod and a second braking device of the release mechanism interactively connected to each other by a non-positive connection.

The trigger unit comprises an actuator button 102 and an actuator 80 connected to each other. The cover unit comprises a delivery member cover 20 and an actuator sleeve 110 connected to each other, wherein the actuator sleeve is coaxially and slidably arranged on the actuator 80. The release mechanism comprises annular inwardly directed ledges 86 on flexible tongues 90 of the actuator 80, and recesses 62 on the outer surface of the plunger rod 60 arranged to be engaged with each other for holding the drive unit in a preloaded state in which the drive unit is connected to the carrier by a carrier driver 68.

FIGS. 1-6 show exemplary embodiments of a medicament delivery device according to the present invention.

The device shown in FIG. 1 comprises an elongated housing formed by a generally tubular proximal housing 12 and a distal housing 124 of a generally tubular shape, but not restricted to it. The proximal housing comprises elongated openings 14 for viewing a medicament container 16, FIG. 1, and a somewhat narrowing proximal end.

The shown medicament container 16 is a syringe with a medicament delivery member in the form of an integrated injection needle. It is however to be understood that other types of medicament containers may be employed within the scope of the present invention as well as other types of medicament delivery members such as mouth or nose pieces, nozzles, nebulizers and the like.

The distal end of the proximal housing 12 is arranged with annular recesses 18 on the inner surface. The proximal end of the distal housing has a somewhat lesser outer diameter, corresponding to the inner diameter of the distal end of the proximal housing and provided with a number of annular protrusions 126 which are intended to fit into the corresponding annular recesses 18 on the inner surface of the proximal housing 12. Inside the elongated housing the cover unit is slidably arranged. The delivery member cover 20 is generally tubular with a first proximal part 22 having a certain diameter and a second distal part 24 having a diameter larger than the proximal part 22, where these parts are joined by an intermediate conical part 26, FIG. 2. Two opposite elongated grooves 28 are arranged along the delivery member cover for viewing the medicament container. On the inner surface of the conical part a circumferential ledge 30 is arranged. At the circumferential distal end of the delivery member cover two openings 32 are arranged opposite each other, where each opening is arranged with somewhat inwardly projecting, flexible, tongues 34.

Further, the medicament container carrier 36 is arranged inside the delivery member cover in the form of a generally tubular body. The proximal part of the medicament container carrier 36 is arranged with a neck portion 38 of lesser diameter. Adjacent the neck portion cut-outs 40 have been made on either side to form guide surfaces. These surfaces cooperate with corresponding shapes of the inner surface of the delivery member cover 20 in order to obtain a stop device against rotation of the medicament container carrier 36 relative the delivery member cover. The distal end of the medicament container carrier is arranged with two distally directed tongues 42 where each tongue is arranged with an opening 44 and an inwardly directed ledge 46 on the distal edge of each opening. The medicament container carrier is further arranged with radially directed flanges 48 on its inner surface in order to obtain a space between the medicament container carrier inner wall and the medicament container to be placed inside.

At the proximal end of the proximal part of the delivery member cover, a needle protection cap grabber 50 is arranged. It is inserted into the proximal part of the delivery member cover and held there by friction. Inside the cap grabber a metal ring 52 is arranged with sharp pointed tongues 54 directed somewhat inwards and towards the proximal end.

Figure 3:
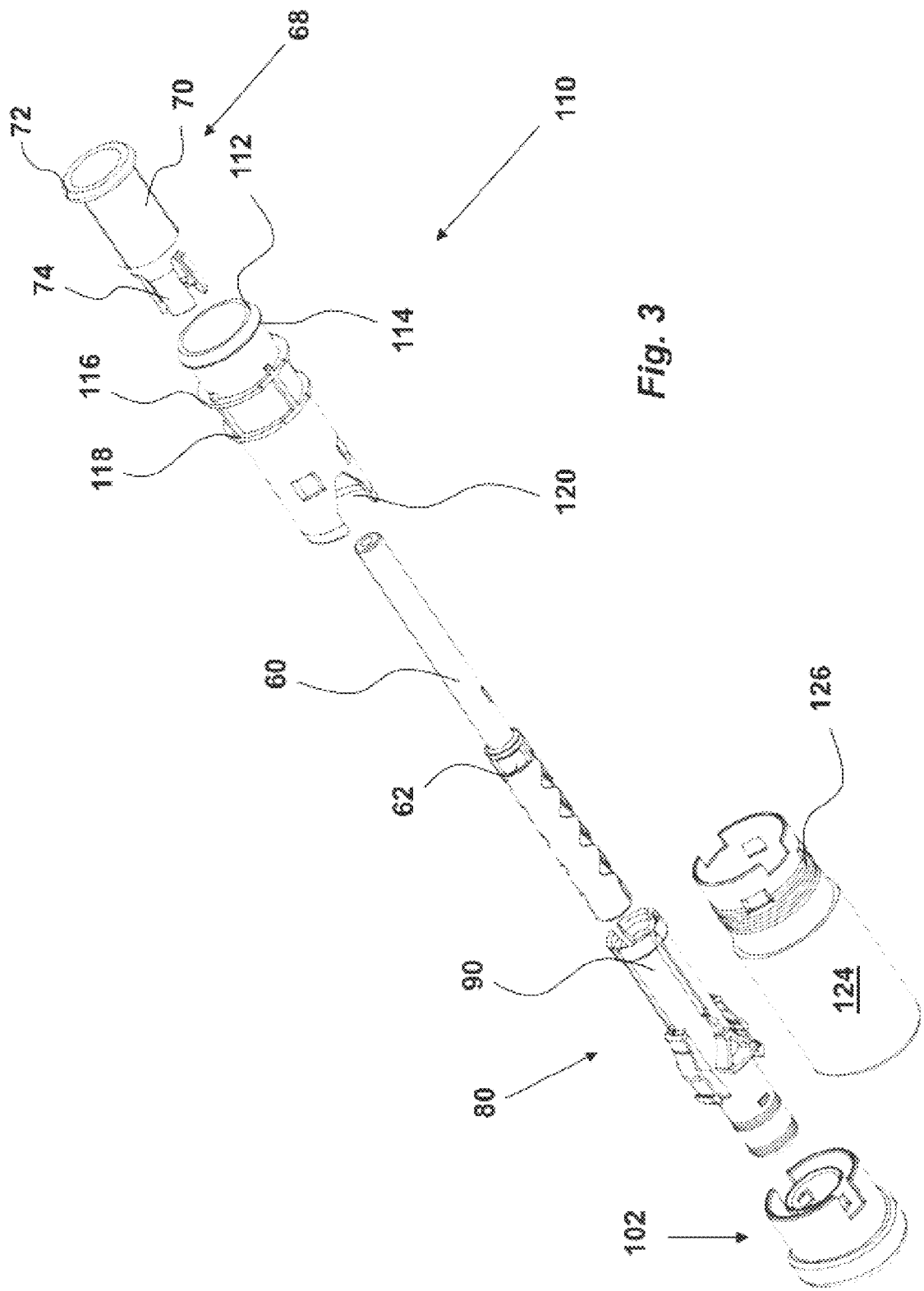
FIG. 3 is an exploded view of a distal part of the device of FIG. 1.
Figure 4:
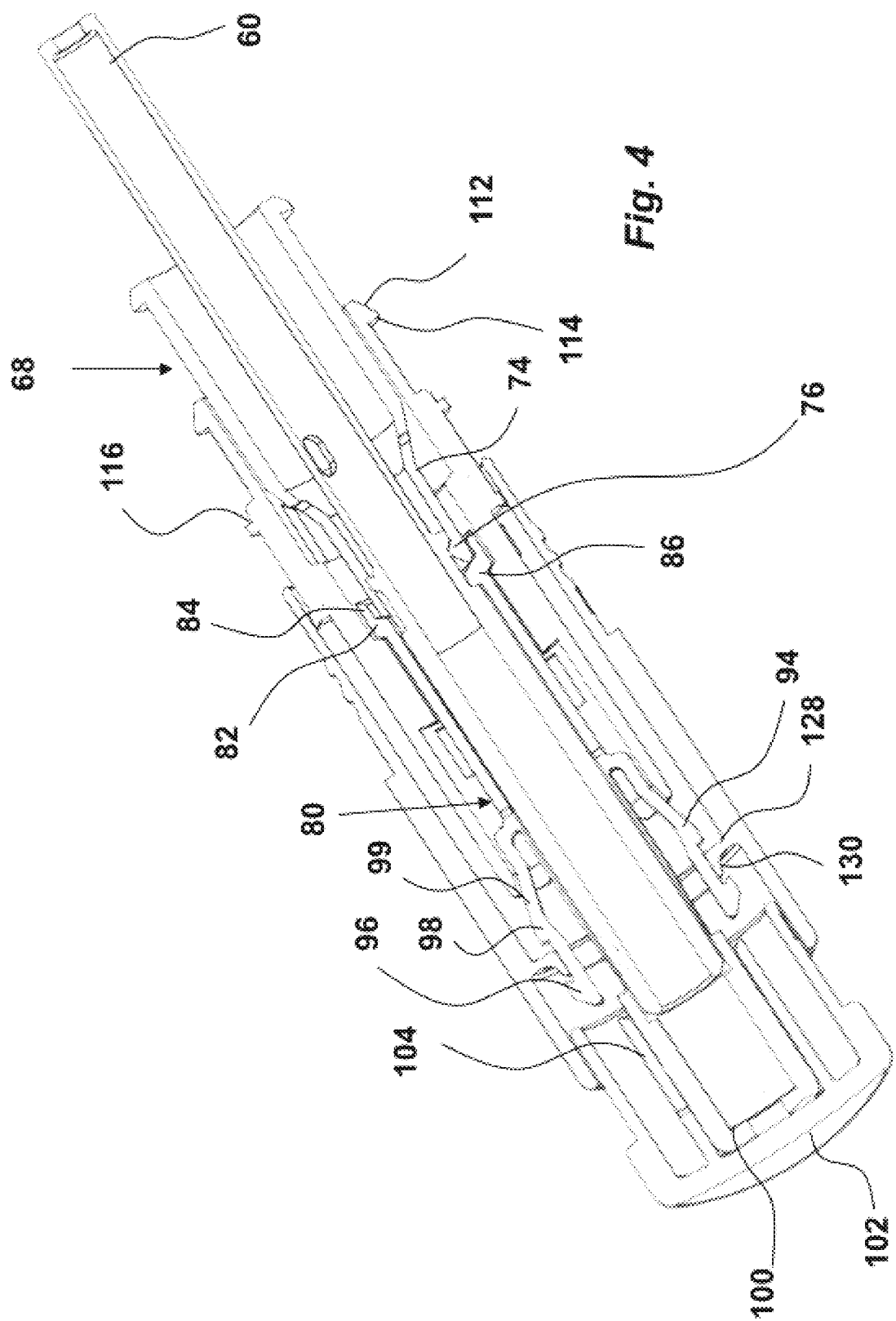
FIG. 4 is a cross-sectional view of the distal part of the device of FIG. 1.

FIGS. 3-4 show a distal part of the device according to FIG. 1. FIG. 3 shows the plunger rod 60 formed as a tube and with an outer diameter somewhat smaller than the inner diameter of the medicament container to be used. The recesses 62 of the plunger rod 60 comprise a certain width and depth. Inside the plunger rod 60 is arranged the drive spring 64 as e.g. a helical compression spring. Adjacent the recesses 62 of the plunger rod 60, the carrier driver 68 is arranged. The carrier driver comprises a tubularly shaped body 70 with an annular ledge 72 and a number of flexible tongues 74 directed towards the distal end of the device, FIG. 3. Each tongue 74 is arranged with inwardly directed ledges 76, FIG. 4, arranged and shaped as to fit into the recesses 62 of the plunger rod 60. Further, the ledges 46 of the medicament container carrier 36 pass behind the annular ledge 72 of the carrier driver 68 such that the container carrier and the carrier driver are connected to each other As seen in FIG. 4, the actuator 80 with a mainly tubular shape is coaxially arranged surrounding the plunger rod 60. A number of longitudinally directed cut-outs 88 are arranged at the proximal part of the actuator so as to form flexible tongues 90, FIGS. 3-5. The proximal end of each flexible tongue 90 has an inclined transition surface 82 which meets with a band-shaped part 84 with enlarged diameter. On the inner surface adjacent each transition surface 82, the annular inwardly directed ledge 86 is arranged, with a shape as to fit into the recesses 62 of the plunger rod 60. The actuator 80 is further provided with two stop ledges 92 directed radially outwards from the outer surface on either side, FIG. 5. Between the stop ledges two flexible tongues 94 are arranged on the outer surface. Each tongue is arranged with an outwardly directed hook 96 at the outer end and a protrusion 98, with an inclined surface 99, a distance along each tongue, FIG. 4. On the inner circumferential surface of the distal housing, an annular ring 128 is arranged, which ring is provided with a circumferential ledge 130 with a shape corresponding to the hooks 96 of the actuator. The upper end of the actuator is arranged with a transversal end wall 100. The actuator button 102 is attached to the upper end of the actuator having two tongues 104 attached and directed in the proximal direction of the device, forming the trigger unit.

The actuator sleeve 110 is coaxially and slidably arranged on the actuator 80. As seen in FIG. 3, the actuator sleeve 110 comprises a proximal end with a conical part 112 ending in a ledge 114 on its outer surface. At a distance from the ledge 114, a first annular ring 116 is arranged the outer surface. A second annular ring 118 is also arranged a further distance from the ledge 114. The distal end of the actuator sleeve is arranged with two oppositely arranged cut-outs 120 of a generally rectangular shape where the widths correspond to the width of the stop ledges 92 of the actuator. A compression spring 122, FIG. 1 a, hereafter named delivery member cover spring surrounds the actuator sleeve 110 and is arranged between the second annular ring 118 of the actuator sleeve and the annular ring 128 on the inner surface of the distal housing. At the circumferential distal end of the delivery member cover two openings 32 are arranged opposite each other, where each opening is arranged with somewhat inwardly projecting tongues. The flexible tongues 34 at the openings 32 of the delivery member cover fit into the circumferential recess formed between the first 116 and the second 118 annular rings of the actuator sleeve, such that the delivery member cover and the actuator sleeve form the cover unit.

According to the invention, the first braking device is at least one groove on the outer surface of the plunger rod and the second braking device is at least one inwardly directed protrusion on the flexible tongues 90 of the actuator 80.

Figure 5:
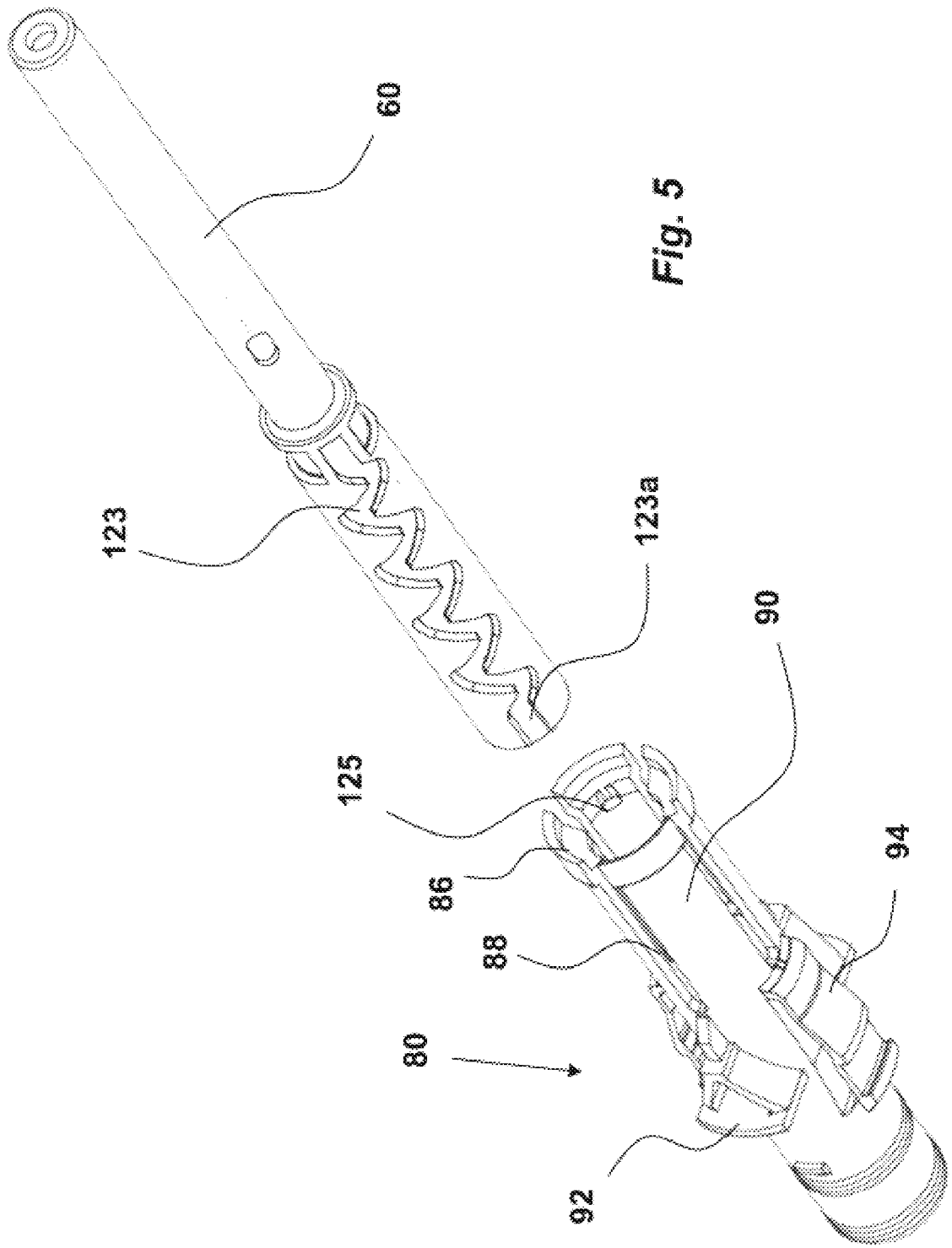
FIG. 5 is a detailed view of one embodiment of the braking mechanism.

According to a first embodiment, the first braking device is at least one groove 123 on the outer surface of the plunger rod 60 with alternating groove sections with inclined directions in relation to the longitudinal direction of the plunger rod, i.e. forming a kind of zig-zag pattern, FIG. 5. Further, according the first embodiment, the second braking device is at least one inwardly directed protrusion 125 on the oppositely positioned tongues 90. The at least one inwardly directed protrusion 125 has a shape which fits into the at least one groove 123 of the plunger rod. The at least one groove 123 has a pitch that can be modified during manufacturing for modifying the speed of the plunger rod.

Figure 6:
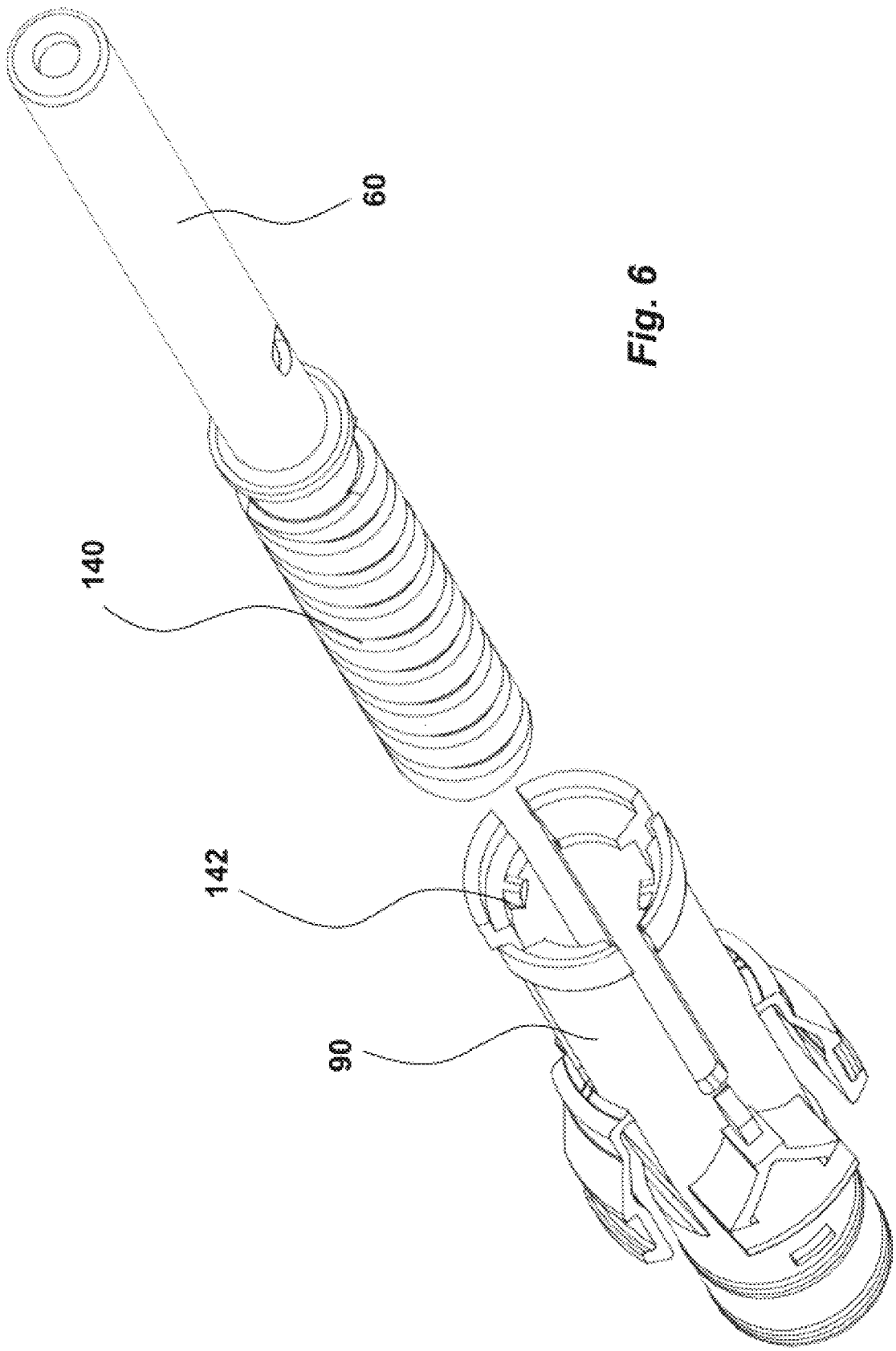
FIG. 6 is a detailed view of another embodiment of the braking mechanism.

According to a second embodiment, the first braking device is at least one groove 140 made as a helically extending groove on the outer surface of the plunger rod, FIG. 6. As with the previous embodiment, the second braking device is at least one inwardly directed protrusion 142 on the oppositely positioned tongues 90. When the plunger rod now moves in the proximal direction during medicament delivery, the protrusions 142 slide along the side surfaces of the helically extending groove 140 and due to the friction, the speed of the plunger rod is lowered. As with the previous embodiment, the speed can be changed by changing the pitch of the helical groove 140 in relation to the longitudinal direction.

Further, the at least one groove 123 of the first embodiment and the helically extending groove 140 of the second embodiment have, at the distal end of the plunger rod, a groove section 123*a* with a direction generally corresponding with the longitudinal direction of the plunger rod, the function of which will be described below.

The plunger rod 60 is held against the force of the compression spring by the release mechanism wherein the inwardly directed ledges 86 of the tongues 90 of the actuator are situated in the recesses 62 of the plunger rod 60 and that the actuator sleeve 110 prevents the tongues 90 from moving radially outwards. Further the ledges 76 of the carrier driver are also arranged into the recesses 62. The hooks 96 of the actuator 80 are adjacent the circumferential ledge 130 as a second safety device.

When a medicament delivery is to be performed the needle protection cap grabber is pulled out of the device. If the actuator button is depressed, without having depressed the cover unit against a delivery site, the hooks 96 of the actuator 80 will be engaged with the circumferential ledge 130 of the distal housing, and will thereby prevent the inwardly directed ledges 86 of the tongues 90 of the actuator from being released from the recesses 62. However, when the proximal end of the cover unit is pressed against a dose delivery site against the force of the compression spring 122, the distal end of the delivery member cover is in contact with the first annular ring 116 of the actuator sleeve 110 and its movement causes the sleeve to move in the distal direction, whereby a part of the proximal end of the band-shaped part 84 is moved outside the proximal end of the actuator sleeve 110. The distally directed edge of the actuator sleeve 110 will then come in contact with the inclined surface 99 of the tongues 94 on the actuator 80 whereby the hooks 96 are moved radially inwards and are free to pass longitudinally inside the circumferential ledge 130.

The next step is to activate the penetration and dose delivery. Should the user however remove the device from the delivery site the compression spring 122 will push the actuator sleeve 110 and thereby the delivery member cover 20 back to its original position and a press on the button will not cause the device to fire. When activating the penetration and dose delivery, the user merely depresses the actuator button 102. This causes the actuator to be moved in the proximal direction whereby the hooks 96 pass inside the circumferential ledge 130 and the band-shaped part 84 moves completely out of the actuator sleeve. The resilient properties of the flexible tongues 90 of the actuator causes the ledges 86 to move out of the groove 62 of the plunger, which then is free to move due to the preloaded spring 64. The penetration stops when the proximal surface of the medicament container carrier 36 abuts the circumferential ledge 30 of the delivery member cover and the ledges 76 of the carrier driver 68 are also moved out of the groove 62 because the arms 74 of the carrier driver are no longer held in place by the band-shaped part of the actuator. I.e. the plunger rod is disconnected from the container carrier and starts to act on the stopper.

However the speed of the plunger rod in the proximal direction is affected by the first and second braking devices due to the friction between the protrusions 125 and the side walls of the groove 123 of the plunger rod 60. In this context it is to be understood that the friction force and thus the speed can be modified by changing the pitch of the groove section in relation to the longitudinal direction.

The force from the compression spring 64 now moves the stopper inside the medicament container 16 and the liquid medicament is delivered to the patient until the stopper reaches the inner proximal end of the medicament container 16, still under the influence of the first and the second braking devices. However, preferably the most proximal groove portion 123a is generally in line with the longitudinal direction of the plunger rod, i.e. there is no braking action at the end of the dose delivery sequence and this is due to that the force of the drive spring decreases when it is expanding during penetration and subsequent dose delivery such that the force at the end of the dose delivery sequence is so low that no braking action is necessary.

When the plunger rod 60 has moved the stopper to the proximal end of the medicament container, its distal end has passed the ledges 86 of the actuator 80 and the tongues 90 are moved inwards. Because the compression spring 64 is also acting on the actuator 80, the actuator 80 is moved inside the actuator sleeve 110. Because of this and because the delivery member cover spring 122 is acting on the actuator sleeve 110 it is urged in the proximal direction. When now the device is removed from the medicament delivery site, the force of the delivery member cover spring 122 pushes the actuator sleeve 110 and thus the delivery member cover 20 connected to it in the proximal direction, whereby the delivery member cover 20 is pushed out of the proximal end of the device and surrounds the medicament delivery member. The movement of the actuator sleeve causes the band-shaped part 84 of the actuator 80 to pass ribs arranged on the inner surface of the actuator sleeve. These ribs prevent any attempts to push the delivery member cover back into the device because the ribs will abut the proximal end of the band-shaped part 84 of the actuator 80. The delivery member cover is thus locked.

Figure 7:
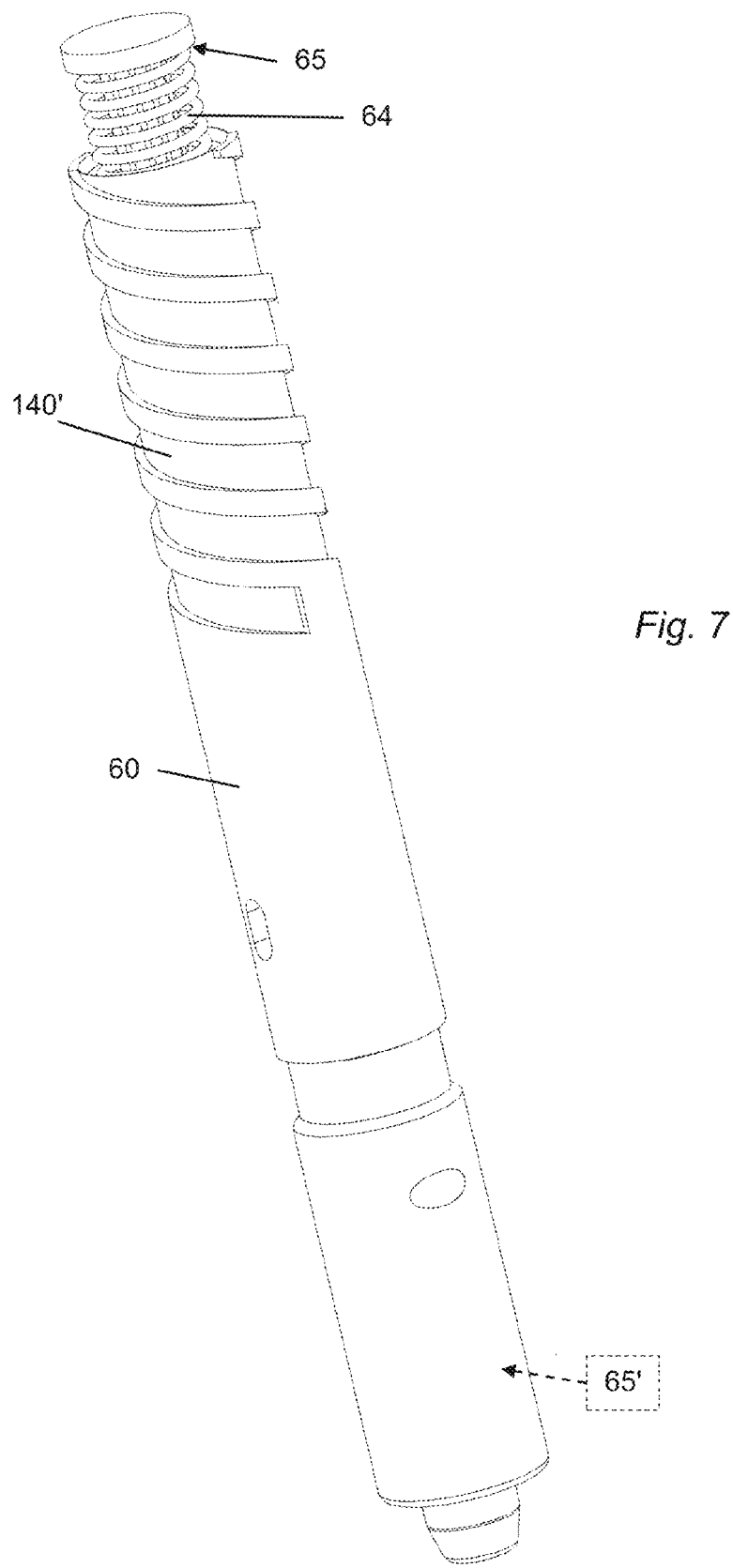
FIG. 7 is a detailed view of yet another embodiment of the braking mechanism.

A third embodiment of the invention is depicted in FIG. 7. In the third embodiment, which is similar to the second embodiment depicted in FIG. 6, the braking mechanism includes a helically extending groove 140' on the outer surface of the plunger rod 60 and at least one inwardly directed protrusion 142 on the oppositely positioned tongues 90 of the actuator 80. In addition, the helically extending groove 140' is formed with a winding direction, i.e., either clockwise or counterclockwise, that is opposite to the winding direction of the helical drive spring 64 that can be disposed inside the plunger rod 60 as described above and depicted in FIG. 7.

When the plunger rod 60 moves in the proximal direction during medicament delivery, the plunger rod rotates and the at least one inwardly directed protrusion 142 (see FIG. 6) slides along the side surfaces of the helically extending groove 140' and due to the friction, the speed of the plunger rod is lowered. As with previously described embodiments, the speed can be changed by changing the pitch of the helically extending groove 140' in relation to the longitudinal direction. In addition, by winding the helically extending groove 140' in the opposite direction of the drive spring 64, the plunger rod 60 interacts with the spring 64.

A way the rod interacts with the spring is through a sharp edge or tang 65, 65' included on at least one of the lowest, or most proximal, coil of the spring 64 and the highest, or least proximal, coil of the spring 64. The tang 65' is indicated by a dashed line as it is hidden in FIG. 7. The spring and at least one tang are such that when the plunger rod 60 rotates, at least one of an area at or near the bottom, or most proximal, inner wall of the plunger rod and an area at or near the top, or least proximal, inner wall of the plunger rod contacts a sharp edge or tang of the spring 64. A result of the contact or contacts is that the edge or tang 65, 65' digs into or grips the plunger rod 60, which may be made of plastic, thereby effectively slowing down the rotation of the plunger rod. It is currently believed that it is preferable that the spring 64 generally should have sharp edges at both its ends and should not otherwise touch the interior wall of the plunger rod 60, leaving some clearance between them, except for possible minor contact, such as due to buckling of the spring.

Further as with the first and second embodiments, the helically extending groove 140' can have, at the distal end of the plunger rod 60, a groove section 123a with a direction generally corresponding with the longitudinal direction of the plunger rod 60.

It is to be understood that the embodiments described above and shown in the drawings is to be regarded only as a non-limiting example of the invention and that it may be modified in many ways within the scope of the patent claims.

What is claimed is:

1. A medicament delivery device, comprising:
   an elongated housing;
   a carrier configured to house a medicament container to which a medicament delivery member is attached, wherein the carrier is slidably accommodated within the housing;
   a trigger unit, comprising an actuator button and an actuator connected to each other;
   a cover unit coaxially and slidably disposed in the housing;
   a release mechanism configured to be actuated partly by the operation of the trigger unit and partly by movement of the cover unit;
   a preloaded drive unit releasably connected to the carrier and controlled by the release mechanism for advancing the carrier to a predetermined proximal position in relation to the housing, wherein the preloaded drive unit comprises a plunger rod and a helical drive spring disposed within the plunger rod; at least one end of the helical drive spring is configured to interact with an interior of the plunger rod; and when the carrier reaches the predetermined proximal position, the drive unit becomes disconnected from the carrier for advancing a slidable stopper within the container and thereby dispensing the medicament; and a braking mechanism between the preloaded drive unit and the release mechanism configured to control a speed of the preloaded drive unit when advancing the slidable stopper within the container, wherein the braking mechanism comprises:

a helical groove on an outer surface of the plunger rod; and at least one inwardly directed protrusion of the actuator interactively connected to the helical groove by a non-positive connection such that advancement of the carrier to the predetermined position causes rotation of the plunger rod;

wherein a winding direction of the helical groove is opposite to a winding direction of the helical drive spring.

2. The medicament delivery device of claim 1, wherein the cover unit comprises a delivery member cover and an actuator sleeve connected to each other, and the actuator sleeve is coaxially and slidably arranged on the actuator.

3. The medicament delivery device of claim 2, wherein the release mechanism comprises annular inwardly directed ledges on flexible tongues of the actuator and recesses on the outer surface of the plunger rod configured to engage each other for holding the drive unit in a preloaded state, in which the drive unit is connected to the carrier by a carrier driver.

4. The medicament delivery device of claim 3, wherein the at least one inwardly directed protrusion is disposed on the flexible tongues of the actuator.

5. The medicament delivery device of claim 1, wherein the helical groove has a pitch that when modified during manufacturing modifies a rotation speed of the plunger rod.

6. The medicament delivery device of claim 5, wherein a section of the helical groove at a proximal end of the plunger rod has a direction that is generally parallel with a longitudinal direction of the plunger rod.

7. The medicament delivery device of claim 1, wherein the at least one end of the helical drive spring includes a tang that interacts with the interior of the plunger rod such that when the plunger rod rotates, the tang contacts the interior of the plunger rod.

8. The medicament delivery device of claim 7, wherein each end of the helical drive spring includes a respective tang.

* * * * *